US00PP10015P

United States Patent [19]

Meilland

[11] Patent Number: Plant 10,015

[45] Date of Patent: Sep. 2, 1997

[54] MINIATURE ROSE PLANT NAMED 'MEISHULO'

[75] Inventor: Alain A. Meilland, Antibes, France

[73] Assignee: The Conard-Pyle Company, West Grove, Pa.

[21] Appl. No.: 706,496

[22] Filed: Sep. 4, 1996

[51] Int. Cl.[6] ..... A01H 5/00

[52] U.S. Cl. ..... Plt./10.1

[58] Field of Search ..... Plt./7.1, 9, 10.1, Plt./10

[56] References Cited

U.S. PATENT DOCUMENTS

P.P. 9,108 4/1995 Olesen et al. ..... Plt./10.1

*Primary Examiner*—Howard J. Locker

*Attorney, Agent, or Firm*—Burns, Doane, Swecker & Mathis, L.L.P.

[57] ABSTRACT

A new and distinct variety of rose plant of the miniature class is provided which abundantly and substantially continuously forms attractive Mandarin Red blossoms. Such blossom coloration tends to be very stable. The plant is erect and exhibits a compact and regular growth habit. The blossoms possess no fragrance. The plant can be grown on its own roots as attractive ornamentation in the landscape or as a decorative pot plant.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) of the new variety was the 'Meichanso' variety (non-patented in the United States). The male parent (i.e., the pollen parent) of the new variety was the product of the pollination of the 'Meilarco' variety (U.S. Pat. No. P.P. 6,170) and the 'Korwerk' variey (non-patented in the United States). The parentage of the new variety can be summarized as follows:

('Meichanso'×('Meilarco'×'Korwerk').

The seeds resulting from the above pollination were sown and small plants were obtained which were physicaly and biolgically different from each other. Selective study resulted in the identification of a single plant of the new variety.

It was found that the new variety of miniature rose plant of the present invention possesses the following combination of characteristics:

(a) forms in abundance attractive double flowers which are Mandarin Red in coloration,
(b) exhibits an erect, compact, and regular grown habit,
(c) forms attractive semi-glossy foliage, and
(d) is particularly suited for growing on its own roots as an ornamental pot plant.

The Mandarin Red flowers are very stable in coloration.

The new variety well meets the needs of the horticultural industry. It is particularly well-suited for use as attractive ornamentation in the landscape or for growing as a decorative pot plant.

The new variety has been found to undergo asexual propagation in France by a number of routes, including budding, grafting, and cuttage. Asexual propagation by the above-mentioned methods as performed in France has shown that the characteristics of the new variety are strictly transmissible from one generation to another.

The new variety has been named the 'Meishulo' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during April while growing on their own roots indoors at Le Cannet des Maures, Var, France. Dimensions in centimeters are shown at the bottom of the photograph.

FIG. 1—illustrates a specimen of a young shoot;

FIG. 2—illustrates a specimen of a cluster of floral buds before the opening of the sepals;

FIG. 3—illustrates specimens of two floral buds at the opening of the sepals;

FIG. 4—illustrates specimens of two floral buds at the opening of the petals;

FIG. 5—illustrates specimens of two flowers during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets with the upper surface being shown at the left and the under surface being shown at the right;

FIG. 15—illustrates specimens of leaves with five leaflets with the upper surface being shown at the bottom and the under surface being shown at the top; and FIG. 16—illustrates specimens of leaves with seven leaflets with the upper surface being shown at the bottom and the under surface being shown at the top.

DETAILED DESCRIPTION

Figures 1, 2, 3, 4, 5, 6, 7, 8, 9, 10, 11, 12, 13, 14, 15, 16:
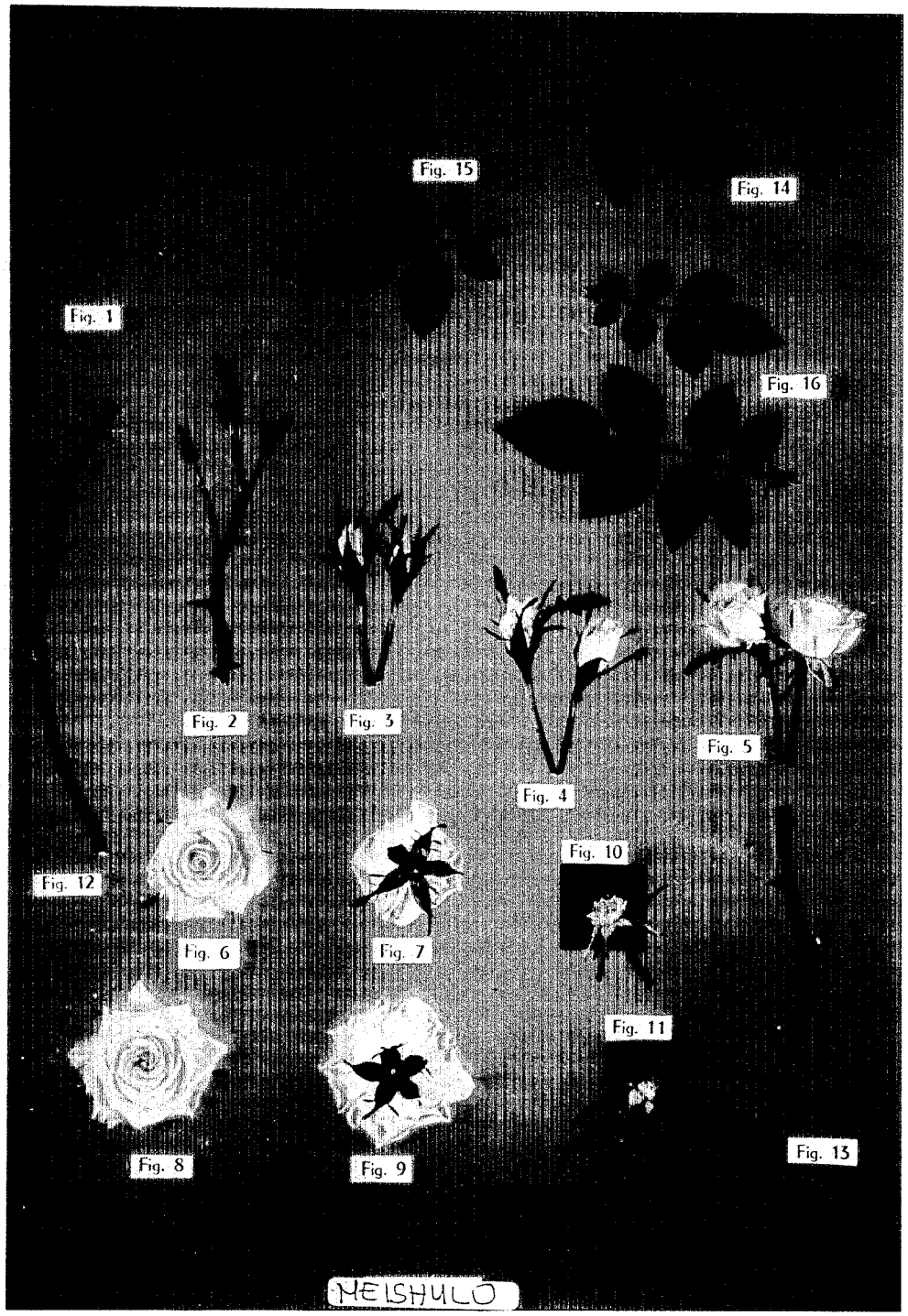

The chart used in the identification of the colors is that of The Royal Horticultural Society (R.H.S. Colour Chart). The terminology which precedes reference to the chart has been added to indicate the corresponding colors in more common terms. The description is based on one year-old specimens of the new variety which were observed during September while growing on their own roots indoors at Le Cannet des Maures, Var, France.

Class: Miniature.

Plant:

*Height.*—Approximately 35 cm. on average at the end of the growing season.

*Habit.*—Erect.

Branches:

*Color.*—Young stems: Lettuce Green, Yellow-Green Group 144A, and lightly suffused with reddish brown. Adult wood: light green, Green Group 137C.

*Thorns.*—Size: small. Quantity: numerous. Color: pinkish.

Leaves:

*Petioles.*—Upper surface: striped, reddish on young foliage and medium green on mature foliage with glandular edges. Under surface: light green and bear some small thorns.

*Stipules.*—Adnate, pectinate, rather narrow and linear.

*Leaflets.*—Number: 3, 5, and 7 (most often). Shape: elliptic. Texture: consistent. General appearance: dense, medium green, and semi-glossy foliage. Color (young foliage): Uper surface: Lettuce Green, Yellow-Green Group 144 A and lightly suffused and edged with reddish-brown coloration. Under surface: Lettuce Green, Yellow-Green Group 144A and suffused with reddish-brown coloration. Color (adult foliage): Upper surface: dark green, Yellow-Green Group 147A. Under surface: Greyed-Green Group 191A and suffused with reddish coloration.

Inflorescence:

*Number of flowers.*—Multiflorous, and commonly with approximately 2 to 5 flowers per stem.

*Peduncle.*—Medium green in coloration, smooth, and the length is approximately 3 cm. on average.

*Sepals.*—Upper surface: tomentose and greenish in coloration. Under surface: medium green.

*Buds.*—Shape: egg-shaped. Length: approximately 1.5 cm. on average. Size: medium. Color upon opening: Upper surface: near Dutch Vermilion, Red Group 40A. Under surface: near Azalea Pink, Red Group 41C.

*Flower.*—Form: elongated cup-shaped. Diameter: approximately 5 cm. on average. Color (when opening begins): Upper surface: near Azalea Pink, Red Group 41C. Under surface: near Mandarin Red, Red Group 41D. Color (when blooming): Upper surface: near Azalea Pink, Red Group 41C. Under surface: near Mandarin Red, Red Group 41D, commonly with some whitening on the external petals. Color (at end of blooming): Upper surface: near Mandarin Red, Red Group 41D. Under surface: near Mandarin Red, Red Group 41D, commonly with some whitening on the external petals. Fragrance: none. Petal number: approximately 35 on average. Petal shape: the base is obtuse, and the tip is oval with reflexed edges. Petal drop: good with the petals commonly detaching cleanly. Anthers: normal and ochre in coloration. Stamen number: approximately 60 on average. Filaments: normal and yellowish in coloration. Pistil number: approximately 50 on average. Stigmas: greenish in coloration. Styles: greenish in coloration. Receptacle: medium green, smooth, and in longitudinal section in the shape of a pitcher.

Development:

*Vegetation.*—Strong.

*Blooming.*—Abundant and substantially continuous.

*Resistance to diseases.*—Good.

I claim:

1. A new and distinct variety of miniature rose plant characterized by the following combination of characteristics:

(a) forms in abundance attractive double flowers which are Mandarin Red in coloration,
(b) exhibits an erect, compact, and regular growth habit,
(c) forms attractive semi-glossy foliage, and
(d) is particularly suited for growing on its own roots as an ornamental pot plant, substantially as herein shown and described.

* * * * *

MEISHULO